United States Patent [19]
Yoon

[11] Patent Number: 5,478,353
[45] Date of Patent: Dec. 26, 1995

[54] SUTURE TIE DEVICE SYSTEM AND METHOD FOR SUTURING ANATOMICAL TISSUE PROXIMATE AN OPENING

[76] Inventor: InBae Yoon, 2101 Highland Ridge Dr., Phoenix, Md. 21131

[21] Appl. No.: 276,671

[22] Filed: Jul. 18, 1994

Related U.S. Application Data

[60] Continuation-in-part of Ser. No. 719,281, Jun. 25, 1991, Pat. No. 5,366,459, which is a division of Ser. No. 450,301, Dec. 15, 1989, Pat. No. 5,100,418, which is a continuation-in-part of Ser. No. 49,504, May 14, 1987, abandoned.

[51] Int. Cl.⁶ ................................................. A61B 17/04
[52] U.S. Cl. ..................... 606/213; 606/104; 606/216; 606/220; 606/151
[58] Field of Search ..................... 606/151, 104, 606/213, 215, 216, 219, 220

[56] References Cited

U.S. PATENT DOCUMENTS

| | | |
|---|---|---|
| 3,827,277 | 8/1974 | Weston . |
| 3,874,042 | 4/1975 | Eddleman et al. . |
| 3,882,854 | 5/1975 | Hulka et al. . |
| 4,064,881 | 12/1977 | Meridith . |
| 4,394,864 | 7/1983 | Meridith . |
| 4,414,721 | 11/1983 | Hufnagel . |
| 4,449,531 | 5/1984 | Cerwin et al. . |
| 4,476,865 | 10/1984 | Failla et al. . |
| 4,686,983 | 8/1987 | Leisman et al. . |
| 4,924,866 | 5/1990 | Yoon . |
| 4,932,962 | 6/1990 | Yoon et al. . |
| 4,935,027 | 6/1990 | Yoon . |
| 4,981,149 | 1/1991 | Yoon et al. . |
| 5,021,059 | 6/1991 | Kensey et al. . |
| 5,047,047 | 9/1991 | Yoon . |
| 5,053,047 | 10/1991 | Yoon . |
| 5,062,846 | 11/1991 | Oh . |
| 5,074,874 | 12/1991 | Yoon et al. . |
| 5,100,418 | 3/1992 | Yoon et al. . |
| 5,104,399 | 4/1992 | Lazarus ................................. 606/153 |
| 5,222,508 | 6/1993 | Contarini . |
| 5,222,976 | 6/1993 | Yoon . |
| 5,258,000 | 11/1993 | Gianturco ............................... 606/151 |
| 5,320,632 | 6/1994 | Heidmueller .......................... 606/144 |
| 5,330,503 | 7/1994 | Yoon ...................................... 606/223 |
| 5,364,408 | 11/1994 | Gordon ................................. 606/144 |
| 5,366,459 | 11/1994 | Yoon ...................................... 606/151 |
| 5,368,601 | 11/1994 | Sauer et al. ........................... 606/144 |
| 5,374,275 | 12/1994 | Bradley et al. ....................... 606/144 |

*Primary Examiner*—Gary Jackson

[57] ABSTRACT

An applicator for suturing openings such as puncture sites in anatomical tissue applies a suture tie device having at least two outwardly turned hooks to penetrate the tissue proximate the opening. A stem, and a plurality of legs extending distally and radially outward from the stem, support the hooks and together with a collar movable along the stem and legs allow the hooks to be gathered radially inward after penetrating the tissue. The suture tie device can be disposed within a tubular housing dimensioned to fit within an endoscopic portal or cannula or for insertion directly through the opening in the anatomical cavity. A rod is disposed within the housing and connected to a proximal end of the stem of the suture tie device. An elongate tubular member is disposed between an inner circumference of the tubular housing and the rod proximally of the collar to move the collar along the stem and to gather the plurality of legs radially inward.

39 Claims, 7 Drawing Sheets

SUTURE TIE DEVICE SYSTEM AND METHOD FOR SUTURING ANATOMICAL TISSUE PROXIMATE AN OPENING

This application is a continuation-in-part of patent application Ser. No. 719,281, filed on Jun. 25, 1991, (now U.S. Pat. No. 5,366,459), which is a divisional application of Ser. No. 450,301, filed Dec. 15, 1989 (now issued as U.S. Pat. No. 5,100,418), which in turn is a continuation-in-part of patent application Ser. No. 49,504, filed May 14, 1987 (now abandoned), the disclosures of all said prior applications incorporated herein by reference.

BACKGROUND OF THE INVENTION

1. Field of the Invention

The present invention relates generally to medical procedures and instruments and, more particularly, to a suture tie device system and method for suturing anatomical tissue proximate an opening.

2. Description of the Background Art

Endoscopic and minimally invasive medical procedures, such as laparoscopy, have become widely accepted for surgery and diagnosis due to the associated advantages relating to reduced trauma and hospitalization time. The performance of an endoscopic procedure, however, requires the creation of one or more puncture sites through a wall of an anatomical cavity to permit introduction of instruments such as portal sleeves or cannulas, endoscopes, ligating appliers, forceps, cauteries and the like into the anatomical cavity. The puncture sites are normally created by means of a penetrating instrument including an obturator, such as a trocar, disposed within a portal sleeve such that, after the penetrating instrument has penetrated into the anatomical cavity, the obturators are withdrawn leaving the sleeves in place to form portals in the cavity wall. Once the endoscopic procedure has been completed, the sleeves are withdrawn and the puncture sites are closed.

Herniation through an improperly closed puncture site in the wall of an anatomical cavity is one of the rare postoperative complications associated with endoscopic procedures that can lead to significant morbidity. With the increased use of endoscopic procedures and the use of larger endoscopic portals an increase in the incidence of such complications can be expected. Even where a defect is small, there is still the possibility of small bowel entrapment in a Richter's type hernia at the site of introduction of the trocar or other penetrating instrument. Hence, it is important that the puncture site be closed or approximated following removal of the endoscopic instruments.

While complications such as herniation and small bowel entrapments can be avoided by suture of the puncture site in the cavity wall, this involves a time consuming and trauma causing procedure whereby the defect in the cavity wall is enlarged and manipulated to provide access for performing suturing of the interior layers, such as the fascia, using standard curved suturing needles and strands of suture material.

Additionally, in other medical procedures, such as anastomosis, bladder reattachment and repair of congenital or non-congenital defects in the wall of an anatomical cavity such as the abdomen, bowel, small blood vessels such as veins and arteries, epidural, pleural and subarachnoid spaces, heart ventricles and spinal and synovial cavities, it is important to quickly and securely repair the opening or separation in the anatomical tissue. In minimally invasive procedures in particular, suturing of the anatomical tissue is both time-consuming and difficult as the suture needles and strands of suture material must be grasped using instruments and manipulated remotely from the operative site through narrow cannulas or sleeves.

SUMMARY OF THE INVENTION

Accordingly, it is a primary object of the present invention to overcome the above mentioned disadvantages of the prior art and to provide a suture tie device having at least two outwardly turned hooks for penetrating anatomical tissue proximate an opening to facilitate repair of the opening by capturing the tissue held by the hooks.

It is another object of the present invention to carry the outwardly turned hooks of the suture tie device on a single leg having a collar movable on the leg in the direction of sharp tissue penetrating tips of the hooks to capture tissue therebetween.

A further object of the present invention is to carry the outwardly turned hooks of the suture tie device on a plurality of radially diverging legs having a collar movable on the legs in the direction of sharp tissue penetrating tips of the hooks to gather the legs and tissue held in the hooks radially inward.

It is yet another object of the present invention to configure the collar and each leg of a suture tie device having at least two outwardly turned hooks to permit distal movement of the collar and to inhibit proximal movement of the collar.

An additional object of the present invention is to form one or more recesses on a distal face of a collar of a suture tie device having at least two outwardly turned hooks to engage sharp tissue penetrating tips of the hooks to form suture loops.

It is still another object of the present invention to provide a variety of applicators for positioning and applying the suture tie device of the present invention.

A further object of the present invention is to penetrate anatomical tissue proximate an opening with sharp tissue penetrating tips of at least two outwardly turned hooks and to capture tissue between the hooks and a collar movable in the direction of the sharp tissue penetrating tips.

Some of the advantages of the suture tie device system and method of the present invention are that the suture tie applicator can be positioned within an anatomical cavity through a cannula or portal sleeve, for example to access an inner surface of a cavity wall surrounding a puncture site, anatomical tissue proximate an opening can be sutured together more rapidly than with standard suturing needles and strands of suture material and without further enlargement or extension of the opening, the suture tie device can be made of bioabsorbable materials and left in the body thereby obviating the need for any subsequent removal procedures, the tension for approximating the tissue proximate the opening can be controlled to facilitate the healing process, and in the case of puncture site closure the possibility of scarring, herniation and other complications is reduced.

The present invention is generally characterized in a suture tie device for suturing anatomical tissue proximate an opening including at least two outwardly turned hooks having sharp tissue penetrating tips, leg means for supporting the outwardly turned hooks, and a collar selectively displaceable along the leg means in the direction of the sharp tissue penetrating tips. The leg means can be a single leg having a proximal portion and distal portion terminating in at least two outwardly turned hooks or a plurality of radially diverging legs each having an outwardly turned distal portion defining one or more of the outwardly turned hooks. The collar has a central opening configured to receive the legs and a plurality of engaging members are formed along at least a portion of an exterior surface of each leg and along an inner surface of the opening to permit distal movement of the collar while inhibiting proximal movement. One or more recesses can be formed in the collar to receive the sharp tissue penetrating tips of the hooks and can be formed with curved walls to cam the tips radially inward.

A further aspect of the present invention is characterized in an applicator for use in applying the suture tie device to anatomical tissue including an elongate tubular housing having a proximal portion and a distal portion for holding the suture tie device, leg controlling means coupled with a proximal end of the legs for controlling proximal and distal movement of the legs, and collar displacing means for selectively displacing the collar along the legs toward the tissue penetrating tips of the hooks.

Another aspect of the present invention is characterized in a method for suturing anatomical tissue proximate an opening including the steps of positioning within the opening a suture tie device with leg means for supporting at a distal end at least two outwardly turned hooks having sharp tissue penetrating tips, penetrating tissue proximate the opening with the sharp tissue penetrating tips of the outwardly turned hooks and moving a collar distally along the leg means towards the sharp tissue penetrating tips of the hooks to capture the tissue held therebetween.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 5 is a side view, partly in section.

DESCRIPTION OF THE PREFERRED EMBODIMENTS

The suture tie device and applicator of the present invention can be utilized to suture closed any type of opening in biological tissue; and, accordingly, while the suture tie device and applicator are described hereinafter for use in closing a puncture site opening after endoscopic procedures, such as laparoscopy, the suture tie device and applicator can also be used to perform anastomosis, reconstructive surgery such as bladder reattachment or to repair a hernia or ruptured bowel or any other congenital or non-congenital separation between tissue segments or openings in a wall of an anatomical cavity, such as the abdomen, small blood vessels such as veins and arteries, epidural, pleural and subarachnoid spaces, heart ventricles and spinal and synovial cavities.

Figure 1:
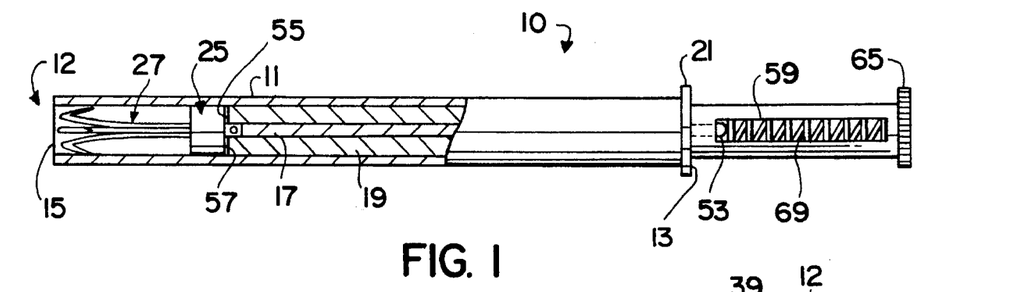
FIG. 1 is a side view, partly in section, of an applicator for application of the suture tie devices of the present invention.
Figure 2:
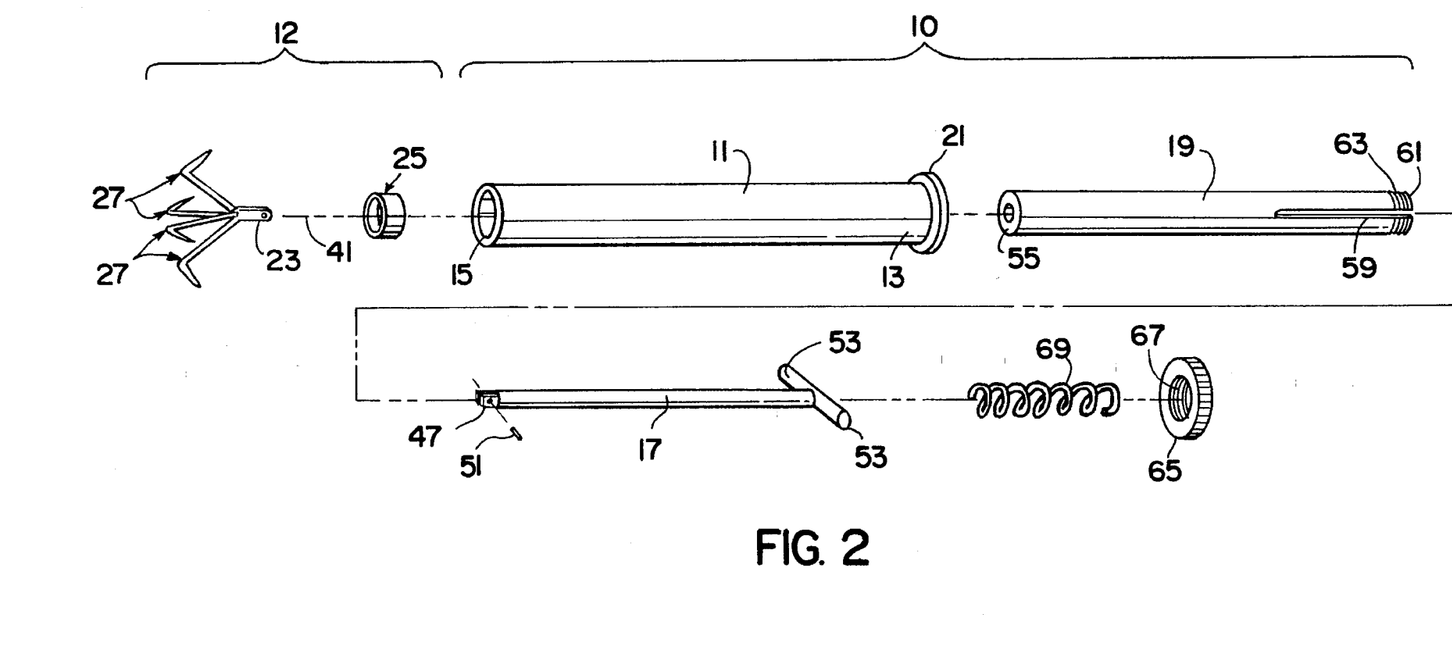
FIG. 2 is an exploded view of the applicator of FIG. 1.

An applicator 10 for applying a suture tie device 12 according to the present invention, as illustrated in FIGS. 1 and 2, includes a tubular housing 11 having open proximal and distal ends 13 and 15, with the suture tie device 12 being disposed within the housing 11 adjacent the open distal end 15, a slender rod 17 connected to a proximal end of the suture tie device 12 and protruding from the proximal end 13 of the tubular housing 11, and an elongated tubular sleeve 19 slidably disposed within the annular region between the inner circumferential surface of the housing 11 and the outer surface of the slender rod 17. The tubular housing 11 is preferably made of a hollow, cylindrical length of stainless steel or other suitable, medically acceptable, plastic or metal material and can be rigid, semi-rigid or flexible and transparent or opaque. An outwardly extending annular flange 21 is formed near the proximal end 13 of the housing 11 and is configured to provide a finger grip for grasping the housing 11. The outer diameter of the tubular housing 11 is dimensioned to allow passage of the housing 11 through a cannula or an incision into anatomical cavities ranging in size from the abdomen to small blood vessels, such as veins and arteries, as well as epidural, pleural and subarachnoid spaces, heart ventricles and spinal and synovial cavities.

Figures 3, 4:
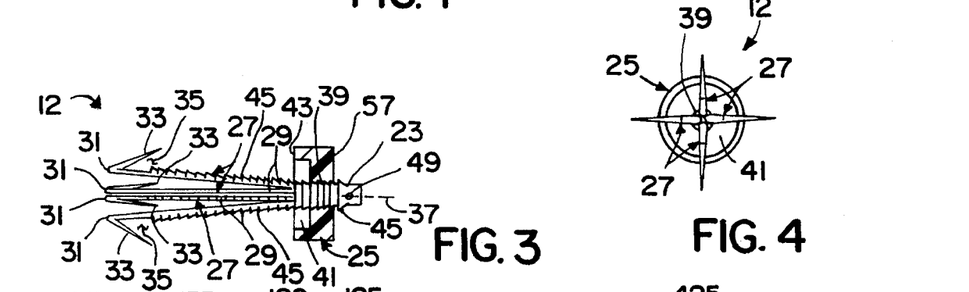
FIG. 3 is an enlarged side view, partly in section, of the suture tie device shown in FIGS. 1 and 2.
FIG. 4 is a frontal view of the suture tie device of FIG. 3.

As best seen in FIGS. 3 and 4, the suture tie device 12 includes a cylindrical stem 23 of relatively large diameter surrounded by a collar 25 and carrying four legs 27 of diminished diameter. Each leg 27 branches distally and radially outward from the stem 23 and has a shaft-like proximal end 29 connected to the stem 23 at a radially divergent angle and an acutely bent distal end 31 terminating in a sharp tissue penetrating tip 33. The bent distal end 31 of each leg 27 forms an outwardly turned hook defining a tissue receiving space 35 with an open side facing proximally toward the collar 25. The legs 27 are arranged symmetrically about the longitudinal axis 37 of the stem 23 to position pairs of tissue penetrating tips 33 at diametrically opposed locations and are preferably configured to form a circular cross-section when gathered together. The stem 23 and legs 27 are completely or partially formed of a bioabsorbable or non-bioabsorbable material, or a combination thereof, which is provided with appropriate physical characteristics so as to be entirely or partially flexible or resilient.

The collar 25 is a solid circular cylinder having an outer diameter to fit within the tubular housing and a central opening or bore 39 configured to slide over the stem 25 and legs 27 in a distal direction to gather the legs 27 radially inward. A concentric cylindrical recess 41 is formed on the distal face 43 of the collar 25 to define a space for receiving the sharp tissue penetrating tips 33 of the legs 27 when gathered. The diameter of the cylindrical recess 41 corresponds approximately to the distance between diametrically opposed tissue penetrating tips 33 of the suture tie device 12 in a gathered state (i.e., with the collar 25 displaced distally forward). The collar 25 is preferably formed as a rigid or semi-rigid member with the central opening 39 extending therethrough longitudinally and having an internal configuration or luminal surface that is configured to cooperate with a plurality of angled teeth or ribs 45 protruding from the outer surface of the stem 23 and legs 27 such that the collar 25 is selectively displaceable only distally, in the direction of the sharp tissue penetrating tips 33 of the legs 27. Individual suture tie devices which make use of a locking/tying member configured to cooperate with a plurality of angled teeth on a leg member are described in U.S. Pat. No. 5,100,418 to Yoon, which is incorporated herein by reference.

The suture tie device 12 is oriented within tubular housing 11 as shown in FIGS. 1 and 2, such that the sharp tissue penetrating tips 33 of the legs 27 face away from distal opening 15 toward collar 25. The radial divergence and length of the legs 27 in the suture tie device 12 are selected so that, together with the radius of curvature of the acutely bent distal end 31, the distance between diametrically opposed tissue penetrating tips 33 of the legs 27 is greater than the outside diameter of the tubular housing 11. Owing to the elasticity of the material used to fabricate the legs 27, confinement of the suture tie device 12 within the tubular housing 11 creates an outward radial bias in the legs 27, such that if the suture tie device 12 is advanced distally relative to tubular housing 11 so as to protrude from the open distal end 15 of the housing 11, the legs 27 will expand radially outward. In other words, the specific configuration of the legs 27 is chosen such that the radial distance from the stem 23 to the sharp tissue penetrating tips 33 of the legs 27 (i.e., the gap width of each hook) is, in a relaxed state, greater than the outer radius of the tubular housing 11.

The slender rod 17 is approximately the same diameter as the stem 23 and has a distal end 47 adapted to couple with the proximal end 49 of the stem 23. The coupled ends 47 and 49 of the rod 17 and stem 23, respectively, are held together with a bio-absorbable frangible pin 51 or by any other medically-acceptable means suitable for releasably connecting the two elements so that the position of the suture tie device 12 can be controlled by manipulation of the rod 17 and the rod 17 withdrawn once the suture tie device 12 is placed in anatomical tissue. The rod 17 extends from the proximal end 49 of the stem 23 to protrude from the proximal end 13 of the tubular housing 11 and terminates proximally in a pair of radially extending arms 53.

The tubular sleeve 19 fits telescopically within the tubular housing 11 to coaxially surround the rod 17 and has a distal face 55 for abutting the proximal face 57 of the collar 25 and a pair of elongated slots 59 defined longitudinally at a proximal end 61 to receive the radial arms 53 of the rod 17. The proximal end 61 of the tubular sleeve 19 is also threaded on an exterior surface 63 to couple with the internal threads 67 of a circular endcap 65. A spring 69 is held in compression between the end cap 65 (which closes the proximal end 61 of the tubular sleeve 19) and the radial arms 53 of rod 17 to bias the proximal end of the rod 17 towards a distalmost position within the elongated slots 59. The distal bias inhibits unintentional proximal movement of the rod 17 and thus maintains the position of the suture tie device 12 relative to the tubular sleeve 19.

The rod 17 and tubular sleeve 19 are preferably made of stainless steel or other suitable, medically acceptable, plastic or metal materials and can be rigid, semi-rigid or elastic. Additionally, all of the foregoing components except the suture tie device 12 can be disposed after use or disassembled for sterilization and reuse.

Figure 5:
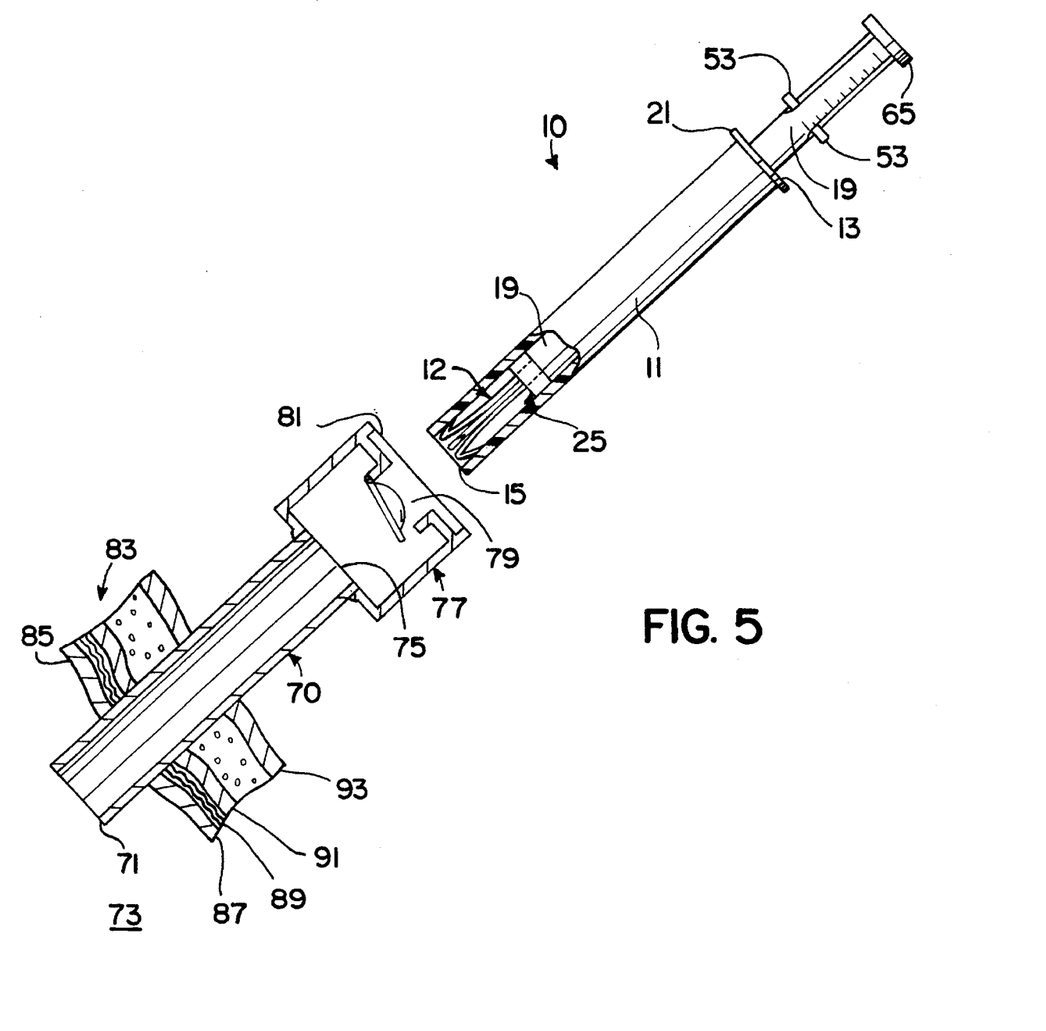
Figure 6:
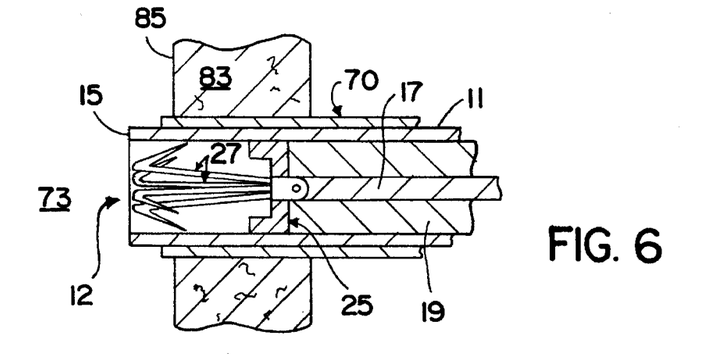
FIGS. 6–10 are broken views, partly in section, illustrating use of the applicator of FIG. 1 for applying a suture tie device to close a puncture site.

The applicator 10 can be employed directly through a puncture site opening or in combination with a portal sleeve to close the puncture site opening. For purposes of illustration, use of the applicator 10 will be described in combination with a portal sleeve inserted into an anatomical cavity through a puncture in the cavity wall formed by a penetrating member, such as a trocar. FIG. 5 shows a portal sleeve 70 having an open distal end 71 positioned within an anatomical cavity 73 and an open proximal end 75 secured to a portal housing 77 externally of the cavity 73. The applicator 10 is inserted into the portal housing 77 through an opening 79 defined in a rear wall 81 of the portal housing 77. The tubular housing 11 of the applicator 10 slides through the portal housing 77 and the portal sleeve 70 into the anatomical cavity 73 as shown in FIG. 6. During the insertion procedure, suture tie device 12 is disposed completely within tubular housing 11 and the legs 27 thereof drawn radially inward owing to the presence of tubular housing 11.

Figure 7:
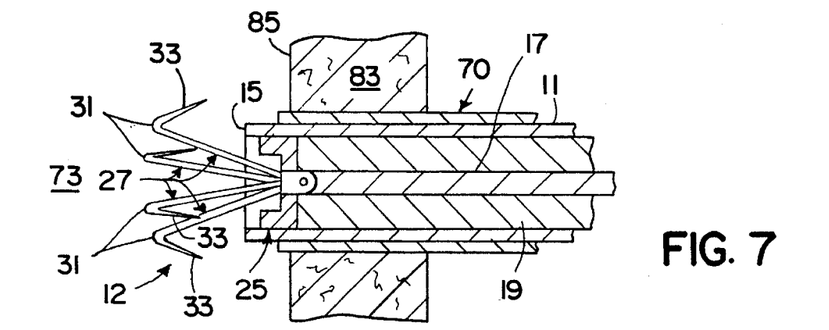

With distal end 15 of tubular housing 11 positioned within anatomical cavity 73, portal sleeve 70 is retracted proximally until almost flush with an inner surface 85 of the cavity wall 83 (e.g., adjacent the peritoneum 87). Tubular housing 11 is also retracted proximally a predetermined distance by exerting a proximal force on the annular flange 21 of the housing 11 while holding the endcap 65 stationary to expose the sharp tissue penetrating tips 33 of the legs 27, as shown in FIG. 7. This can be accomplished, for example, by placing index and middle fingers of one hand on opposite sides of the tubular housing 11 ahead of the annular flange 21 and using the thumb of the hand to hold the endcap 65 stationary while drawing the flange 21 toward the endcap 65. In this manner, the suture tie device 12 is not appreciably moved in either proximal or distal directions.

In the deployed position, the legs 27 of the suture tie device 12 spring radially outward due to elastic energy which is stored during their confinement within tubular housing 11. The sharp tissue penetrating tips 33 of the legs 27 extend radially outward and face proximally toward distal surface 85 of the tissue surrounding the puncture site at a number of locations circumscribing the puncture site opening.

Figure 8:
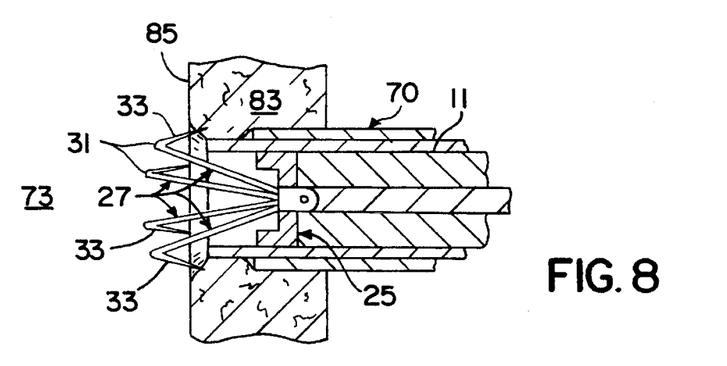

Referring now to FIG. 8, the entire applicator 10 is retracted proximally to cause the proximally-facing, sharp tissue penetrating tips 33 of the legs 27 to penetrate into the cavity wall 83. The amount of penetration depends on the length of the tissue penetrating tips 33 (i.e., the depth of the throat of each hook), and suture tie devices of various lengths can be chosen according to the type of cavity penetrated, the specific layers to be closed or approximated, and the amount of fat and muscle tissue present. Along with the length of the tissue penetrating tips 33 of the legs 27, the radius of curvature of the acutely bent distal end 31 of the legs 27 determines how much tissue of the cavity wall 83 is received in the hook formed by each leg 27.

Figure 9:
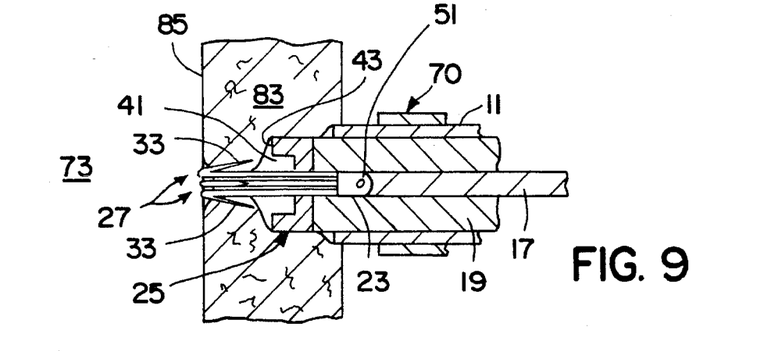

Once the tissue penetrating tips 33 of the legs 27 are positioned in the cavity wall 83, tubular housing 11 and portal sleeve 70 are retracted while the legs 27 and thus the sharp tissue penetrating tips 33 of the legs 27 are gathered radially inward as shown in FIG. 9. This is accomplished, for example, by positioning the index and middle fingers of the hand on opposite sides of the tubular sleeve 11 immediately ahead of the protruding radial arms 53 of the rod 17 and pressing down on the endcap 65 with the thumb of the hand to urge the tubular sleeve 19 and thus the collar 25 distally over the stem 33 and legs 27 of the suture tie device 12 toward the sharp tissue penetrating tips 33. Angled teeth or ribs 45 (see FIG. 3) on the stem 23 and legs 27 prevent proximal movement of the collar 25 so that, once advanced, collar 25 will not loosen. The displacement of the collar 25 along legs 27 controls the tension applied to the tissue surrounding the puncture site to approximate the anatomical tissue adjacent the opening.

Figure 10:
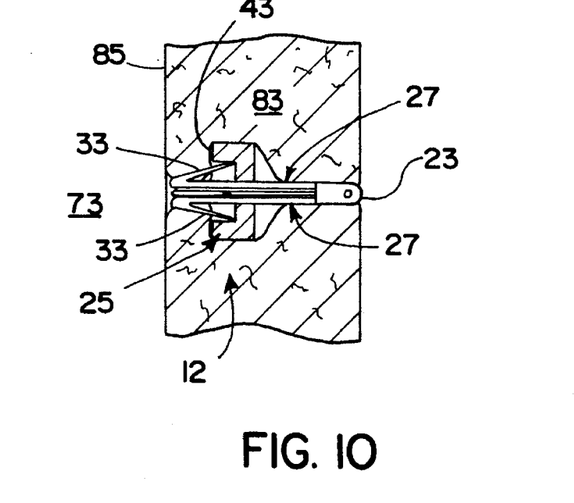

The collar 25 is preferably advanced distally until the sharp tissue penetrating tips 33 of the legs 27 are received in the cylindrical recess 41 on the distal face 43 of the collar 25 forming closed loops holding the tissue which has been gathered. With the collar 25 properly positioned, the rod 17 is released from the stem 23 using a quick tug to break the frangible pin 51 that holds the two together or by any other suitable method of release. FIG. 10 shows an implanted suture tie device 12 within the wall 83 of the anatomical cavity 73. After implantation of the suture tie device 12 to approximate the inner layers (e.g., the peritoneum, muscle and fascial layers 87, 89 and 91 in FIG. 5) of the cavity wall 83, the outer skin layer (element 93 in FIG. 5) can be sutured in the conventional manner and the suture tie device 12 left for absorption by the body over time.

Figure 11:
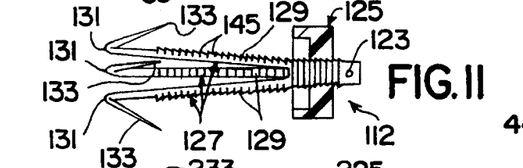
FIG. 11 is a side view of a modified suture tie device according to the present invention.

A modification of the suture tie device 12 is illustrated in FIG. 11 wherein the modified suture tie device 112 includes a stem 123 from which three legs 127 extend distally and radially outward like a tripod. The legs 127 are the same as legs 27 previously described and each have a proximal end 129 connected to the stem 123 at an angle and an acutely angled distal end 131 terminating in a sharp tissue penetrating tip 133 extending proximally and radially outward. While the tissue penetrating tips 33 of suture tie device 12 reside essentially in two perpendicular planes in their distended state, the tissue penetrating tips 133 of suture tie device 112 preferably lie within three oblique planes. Like suture tie device 112, the stem 123 and legs 127 of suture tie device 112 are also formed with angled teeth 145 or the like to couple with a cooperating structure in collar 125 to inhibit proximal movement of the collar 125 while allowing distal movement.

Figure 12:
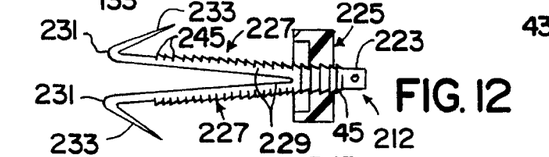
FIG. 12 is a side view of another suture tie device according to the present invention.

Another modification of the suture tie device 12 is illustrated in FIG. 12 with the primary difference being a reduced number of legs. The modified suture tie device 212 includes only two legs 227 which are essentially coplanar and diverge radially from one another in a distal direction before bending acutely backward at a distal end 231 and terminating in sharp tissue penetrating tips 233. The legs 227, stem 223 and collar 225 of suture tie device 212 are essentially the same as the legs 127, stem 123 and collar 125 of suture tie device 112 and the legs 27, stem 23 and collar 25 of suture tie device 12, and are each provided with angled teeth 245 or the like to prevent proximal movement of the collar 225. Hence, suture tie devices 112 and 212 can be directly substituted for suture tie device 12 in the applicator 10 of the present invention.

Figure 13:
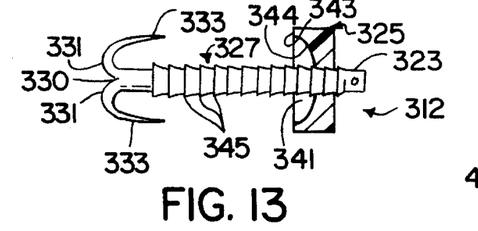
FIG. 13 is a side view of yet another suture tie device according to the present invention.

In a further modification of the suture tie device of the present invention, shown in FIG. 13, the modified suture tie device 312 has a single rigid or semi-rigid leg 327 extending distally from stem 323 and a collar 325 with an annular camming recess 341. The single leg 327 is the same diameter as the stem 323 and branches outward at a distal end 330 into two bent portions or knees 331 from which sharp tissue penetrating tips 333 extend. The collar 325 is configured to fit within tubular housing 11 and has a distal face 343 defining the annular recess 341 with curved sidewalls 344 to form a cam surface for bending the sharp tissue penetrating tips 333 of the device; however, the initial distance between the sharp tissue penetrating tips 333 of the suture tie device 312 and the leg 327 is approximately the same as the radius of the recess 341 in the distal face 343 of the collar 325. Since the collar 325 is approximately the same diameter as the tubular housing 11 and the leg 327 is a rigid or semi-rigid member, the tissue penetrating tips 333 of the suture tie device 312 generally do not elastically and resiliently deform when confined within the housing 11.

Use of the suture tie device 312 of FIG. 13 individually for closing a puncture site is illustrated in FIGS. 14 through 17 wherein only the distal end of the applicator 10 is shown and the steps for exposing the sharp tips 333 of the suture tie device 312 have been omitted; however, it will be appreciated that a similar method can be used to perform anastomosis by applying a plurality of circumferentially spaced suture ties to join abutting tubular walls of anatomical organs or vessels.

Figure 14:
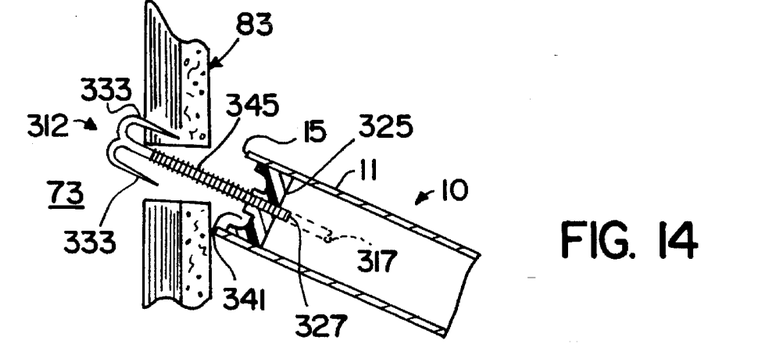
FIGS. 14–17 are fragmentary views, partly in section, illustrating use of the suture tie device of FIG. 13.
Figure 15:
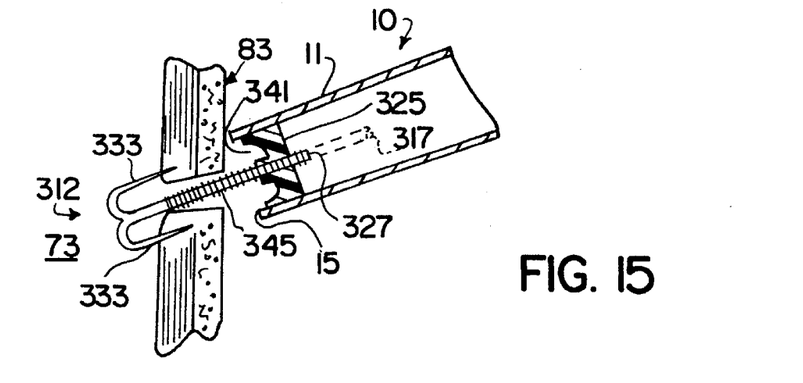
Figure 16:
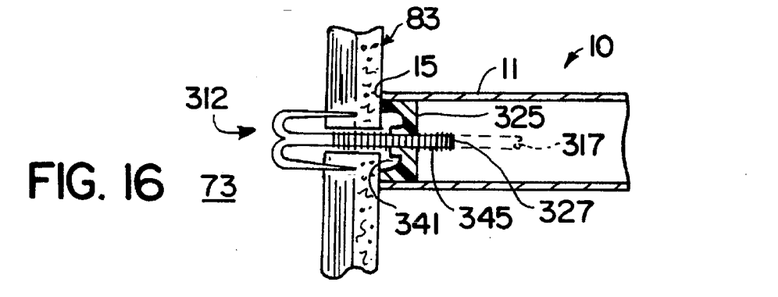
Figure 17:
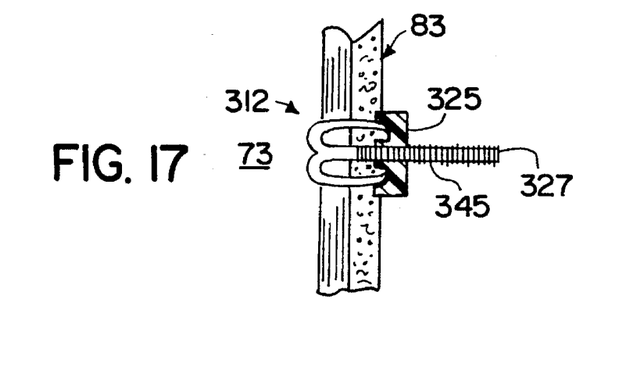

With the collar 325 retained within the tubular housing 11 externally of the cavity wall 83 and the tips 333 exposed within the anatomical cavity 73, the applicator 10 is tilted so that one of the sharp tissue penetrating tips 333 snags tissue on one side of the puncture as shown in FIG. 14. The applicator 10 is then tilted in an opposite direction and manipulated so that the other sharp tissue penetrating tip 333 snags tissue on the opposite side of the puncture as shown in FIG. 15. The tubular housing 11 is then straightened as shown in FIG. 16 and the leg 327 retracted proximally through the collar 325 which is held stationary to pull the tissue penetrating tips 333 through the tissue and toward the collar 325. The cooperating rib and detent structure 345 of the collar 325 and leg 327 prevents the leg 327 from slipping out of the collar 325 or from loosening. As the sharp tissue penetrating tips 333 of the leg 327 move into the recess 341 formed in the collar 325, the tips 333 are cammed radially inward against the curved sidewalls of the recess 341, concomitantly gathering inward the tissue captured between the leg 327 and the sharp tissue penetrating tips 333 to approximate the puncture site opening. The rod 317 is then detached from the stem 323 of the suture tie device 312 in the manner previously described in connection with suture tie device 12, the proximal portion of the suture tie is clipped if desired, and the applicator 10 removed from the site.

In addition to the foregoing modifications, the plural-tipped suture tie device of the present invention can be further modified to incorporate the various aspects of the individual suture ties described in U.S. Pat. No. 5,100,418 to Yoon.

Figure 18:
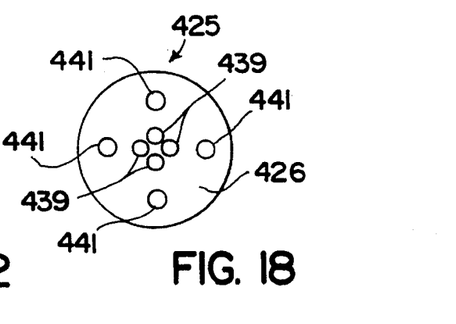
FIG. 18 is an enlarged frontal view of a collar for use in a suture tie device according to the present invention.
Figure 19:
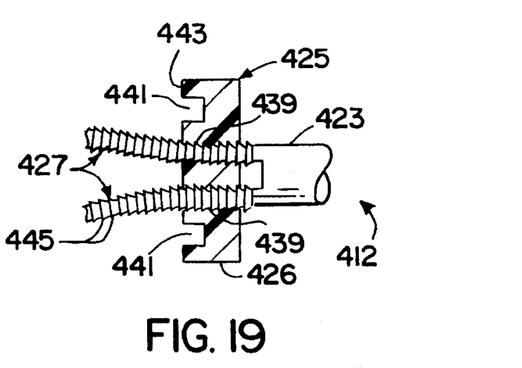
FIG. 19 is a fragmentary view, partly in section, of the collar of FIG. 18 engaging legs of a suture tie device according to the present invention.

A modification of the collar 25 is illustrated in FIGS. 18 and 19 wherein the modified collar 425 has individual apertures or openings 439 for receiving respective legs 427 of a suture tie device 412 similar to suture tie device 12 previously described and individual recesses 441 for receiving the respective tissue penetrating tips of each leg 427.

More particularly, the collar 425 has a cylindrical body 426 with a plurality of closely spaced openings 439 defined near the center of the body 426 and a plurality of annularly spaced recesses 441 radially spaced from the openings on the distal face 443 of the collar 425. Each of the openings 439 in collar 425 is dimensioned to accommodate a single leg 427 of the suture tie device 412 and preferably have an internal configuration or luminal surface that is configured to cooperate with a plurality of angled teeth or ribs 445 protruding from the outer surface of the leg 427 extending therethrough. The collar 425 is initially positioned distally of the stem 423 of the suture tie device 412, as shown in FIG. 19, with the legs 427 of the device extending through the openings 439 in the collar 425 and the recesses 441 each facing a sharp tissue penetrating tip (not shown) of the legs 427.

Figure 20:
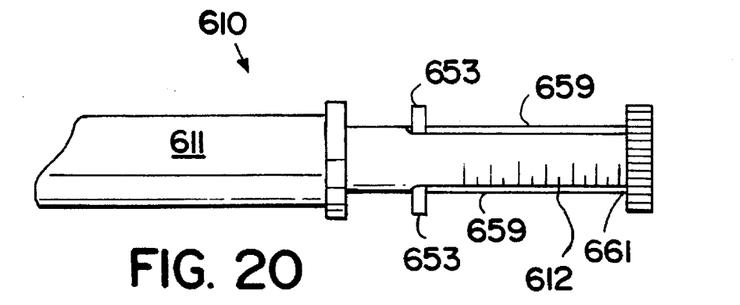
FIG. 20 is a fragmentary side view of the proximal end of the applicator of FIG. 1 showing scale markings on the elongate tubular sleeve.

The applicator 610 illustrated in FIG. 20 is similar to the applicator 101 in the embodiment of FIGS. 1 and 2 with the exception that a scale 612 is marked on an outer surface of the proximal end 661 of the tubular sleeve 619. The tubular sleeve 619 is telescopically fitted within a tubular housing 611 and provided at a proximal end with elongated longitudinal slots 659 through which radial arms 653 of a slender rod (not shown) extend. The scale 612 allows the user to gauge the displacement of the radial arms 653 within the elongated slots 659 to control the displacement of a collar along the stem and legs of a suture tie device (not shown). The amount of distal displacement of the collar on the legs is directly related to the tension applied to the walls of the puncture wound. Hence, the user of the applicator 610 is able to control the tension of the suture tie device with reference to the scale 612 marked on the tubular sleeve 619.

Figure 21:
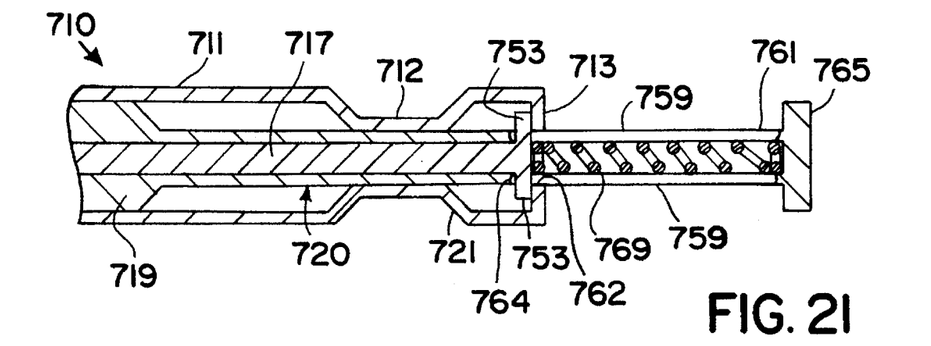
FIG. 21 is a sectional view of the proximal end of a modified applicator according to the present invention.
Figure 22:
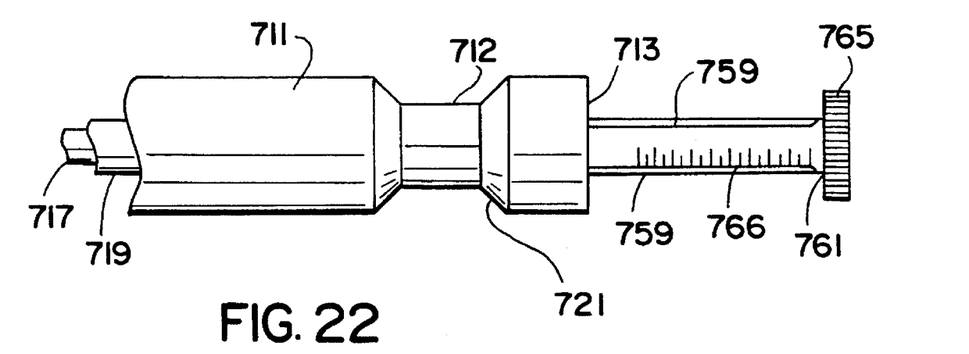
FIG. 22 is a side view of the applicator of FIG. 23.

Another modification of the applicator of the present invention is shown in FIGS. 21 and 22, wherein the applicator 710 is similar to the applicator 10 and has an elongate tubular housing 711 with a reduced diameter portion 712 near a closed proximal end 713 and a rod 717 disposed completely within the housing 711. Specifically, the elongate tubular housing 711 is provided with a finger grip 721 near the proximal end 713 formed by the reduced diameter portion 712 of the tubular housing 711 to facilitate grasping of the tubular housing 711, for example with two fingers placed on opposite sides of the finger grip 721 within the reduced diameter portion 712. An elongate tubular sleeve 719 is similar to tubular sleeve 19 but has a reduced outer diameter portion 720 in the vicinity of the finger grip 721 of the tubular housing 711. The reduced diameter portion 720 of the elongate tubular sleeve 719 extends from the distal end of the finger grip 721 to the proximal end 761 of the sleeve 719, which in turn protrudes through an opening 762 in the proximal end 713 of the tubular housing 711. The rod 717 is telescopically fitted within the sleeve 719 and terminates proximally in a pair of radial arms 753 that extend perpendicularly through a pair of elongated slots 759 defined in the reduced diameter portion 720 of the elongate tubular sleeve 719 near the proximal end 761. The radial arms 753 of the rod 717 are initially positioned at the distal end 764 of the slots 759 against the closed proximal end 713 of the housing 711. Like the applicator 10, the modified applicator 710 has an endcap 765 that closes the tubular sleeve 719 at a proximal end and a spring 769 held in compression between the radial arms 753 of the rod 717 and the endcap 765. A scale 766 is also marked on the proximal end 761 of the tubular sleeve 719 to gage the advancement of a collar on the legs of a suture tie device being implanted.

Only the proximal portions of the applicator 710 have been illustrated in FIGS. 21 and 22; however, it will be appreciated that the distal portions can be formed with any cooperating structure to deliver suture tie devices of the type described herein, such as that shown in FIGS. 1 and 2. For purposes of illustration, reference will be made to the suture tie device of FIG. 1 when explaining operation of the applicator.

In use, the applicator 710 is positioned within a puncture site in the manner previously described in connection with applicator 10 and index and middle fingers of the user are disposed on opposite sides of the finger gripping portion 721 and the thumb of the same hand rested on end cap 765 at the proximal end 761 of tubular sleeve 719 to slide the tubular housing 711 proximally toward end cap 765. Spring 769 exerts a force against rod 717 to prevent proximal movement of the rod 717 as the housing 711 is drawn toward the endcap 765 to expose the sharp tissue penetrating tips 33 of the suture tie device within the anatomical cavity. The entire applicator 710 is then retracted so that the tissue penetrating tips 33 of the suture tie device penetrate the tissue surrounding the puncture site. Exertion of continued pressure on end cap 765 and finger gripping portion 721 causes an inner surface of the finger gripping portion 721 to bear against the radial arms 753 of the rod 717 thereby urging the rod 717 toward the end cap 765 against the bias of spring 769. With reference to FIG. 1, distal movement of the elongate tubular sleeve 719 relative to the rod 717 causes collar 25 to displace distally along the legs 27 of the suture tie device, thereby gathering the legs 27 radially inward to approximate the anatomical tissue adjacent the puncture site opening. The tension applied to the tissue can be gaged using the scale 766 marked on the proximal end 761 of the tubular sleeve 719 and removal of the applicator 710 from the puncture site proceeds as previously described.

Figure 23:
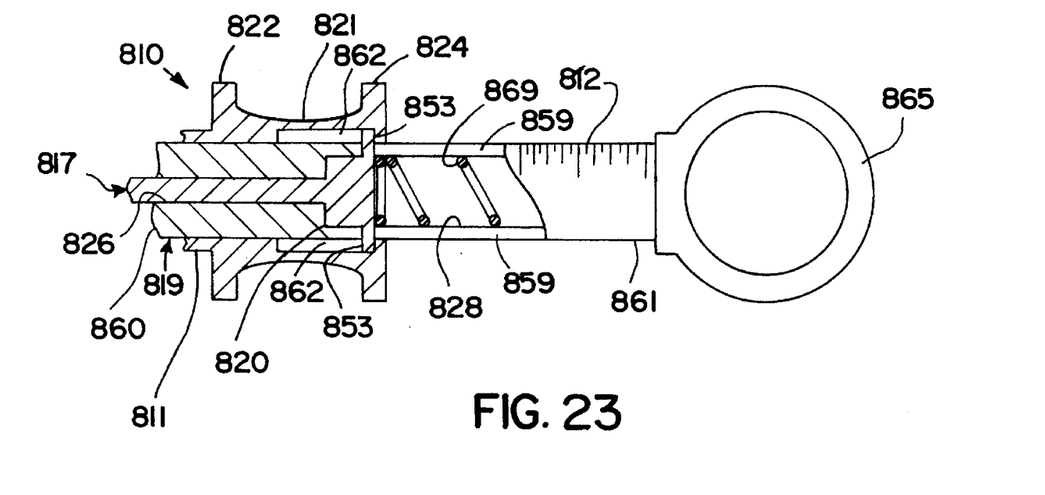
FIG. 23 is a side view, partly in section, of the proximal end of another modified applicator according to the present invention.

Yet another modification of the applicator is illustrated in FIG. 23 wherein a tubular housing 811 is similar to tubular housing 711 with the exception that the finger grip 821 is defined between a pair of longitudinally spaced annular disks 822 and 824, and is rounded to accommodate the index and middle fingers of the user, for example. A tubular sleeve 819 similar to tubular sleeve 19 is disposed within the tubular housing 811 and includes a distal portion 860 having a small diameter bore 826 corresponding approximately to the diameter of a stem portion of the suture tie device to be applied, and a proximal portion 861 having a larger diameter bore 828. A rod 817 is disposed primarily within the small diameter bore 826 of the tubular sleeve 819 and includes an increased diameter portion 820 disposed within the large diameter bore 828 of the tubular sleeve 819. The rod 817 further includes a pair of radial protrusions 853 which project radially outward from an outer surface of the increased diameter portion 820 through slots 859 defined on opposed sides of the tubular sleeve 819 and are received in an annular cavity 862 defined on an interior surface of tubular housing 811, thereby limiting movement of tubular housing 811 relative to the rod 817 in accordance with the length of the cavity 862. A spring 896 is held in compression between a proximal face of the rod 817 and a ring handle 865 which closes the proximal end 861 of the tubular sleeve 819 to normally bias the rod 817 to a distal end of the slots 859. A scale 812 is advantageously marked on an outer surface of the tubular sleeve 819 so that the user may gauge the tension applied to the tissue of the puncture wound by the advancement of the housing 811 relative to the tubular sleeve 812.

From the above, it will be appreciated that the applicator of the present invention can be used to quickly and effectively close a puncture site opening formed by a penetrating member such as a trocar as well as to perform anastomosis, reconstructive surgery such as bladder reattachment or to repair a hernia or ruptured bowel or to suture any other opening formed in anatomical tissue or separating tissue segments. Hence, by "close" or "repair" is meant to approximate or suture together any congenital or non-congenital gaps between tissue segments such as adjacent tubular vessels or disconnected organs and holes or recesses in anatomical tissue such as bowel ruptures, hernias or puncture site openings in a cavity wall. It will also be appreciated that the applicator of the present invention can be inserted into an anatomical cavity through a cannula or portal sleeve as well as directly through an incision or puncture in the wall of an anatomical cavity.

The suture tie of the present invention can have any number of legs that are acutely bent, curved or configured in any way to form one or more tissue penetrating hooks for grasping tissue proximate a puncture site or other opening in anatomical tissue. When the suture tie of the present invention has only one leg, that leg is configured to carry at least two outwardly turned tissue penetrating hooks; and when plural legs are provided, each of the legs can carry one or more outwardly turned tissue penetrating hooks. Any one or all of the stem, proximal and distal ends of the legs, and the collar can be completely or partially formed of a bioabsorbable or non-bioabsorbable material, or a combination thereof, which can be provided with appropriate physical characteristics so as to be entirely or partially rigid, semi-rigid or flexible, elastic, resilient or malleable in accordance with the suture tie device's intended utilization.

Various bioabsorbable or biodegradable materials can be used to make the suture devices of the present invention with the composition determined by the rigidity or flexibility required. Generally, the bioabsorbable materials are thermoplastic polymers such as absorbable polymers and copolymers of poly-dioxanne, lactide, glycolide and the like. Polyglycolic acid is disclosed in U.S. Pat. Nos. 3,463,158; 3,739,773; and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841; 3,564,078 and 3,759,264.

The throat and gap dimensions of the hooked portion each leg (i.e., the depth and width of the tissue receiving space defined by each hook) are chosen to suit the particular procedure to be performed and can be such that the sharp tip of each hook penetrates partially or completely through anatomical tissue such as an anatomical cavity wall to mate with a collar. The collar can have any exterior shape fitting within a tubular housing and can have a continuous or discontinuous distal surface defining one or more recesses or apertures to receive the sharp tissue penetrating tips of the legs. For example, the collar could include a cylindrical body of smaller diameter than the tubular housing of the applicator with recesses being formed in a plurality of tubular members carried by the cylindrical body on radial arms. In those instances where the sharp tissue penetrating tips of the legs are to be received in individual recesses, alignment of the tips with the recesses can, for example, be achieved by providing a cooperating spline and groove arrangement between the opening in the collar and the leg or legs of the suture tie device.

The applicator can be configured to hold a single suture tie device as shown or multiple suture tie devices; and when multiple suture tie devices are to be held, the applicator can be configured in any manner suitable for holding and applying the suture tie devices, including the configurations shown and described in U.S. Pat. No. 5,100,418 to Yoon. Additionally, the housing, rod and sleeve of the applicator can be rigid, semi-rigid or flexible and normally straight or curved for performing different procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A suture tie device for suturing anatomical tissue proximate an opening comprising at least two outwardly turned hooks having sharp tissue penetrating tips;

leg means integral with said hooks for supporting said at least two outwardly turned hooks; and a collar selectively displaceable along said leg means in the direction of said sharp tissue penetrating tips.

2. A suture tie device as recited in claim 1 wherein said leg means is a single leg having a proximal portion and a distal portion terminating in said at least two outwardly turned hooks.

3. A suture tie device as recited in claim 2 wherein said collar has a central opening configured to receive said leg and a plurality of engaging members are formed along at least a portion of an exterior surface of said leg and along an inner surface of said opening to permit distal movement of said collar and to inhibit proximal movement of said collar.

4. A suture tie device as recited in claim 3 wherein at least one recess is formed in said collar to receive said sharp tissue penetrating tips of said outwardly turned hooks.

5. A suture tie device as recited in claim 4 wherein said recess is an annular cavity formed on a distal face of said collar surrounding said central opening.

6. A suture tie device as recited in claim 5 wherein said annular cavity is defined by inwardly curved walls to cam said sharp tissue penetrating tips of said outwardly turned hooks inward.

7. A suture tie device as recited in claim 4 and further comprising a plurality of recesses formed in said collar to receive said sharp tissue penetrating tips of said outwardly turned hooks.

8. A suture tie device as recited in claim 1 wherein said leg means includes a plurality of legs each having an outwardly turned distal portion defining one or more of said outwardly turned hooks.

9. A suture tie device as recited in claim 8 and further comprising a cylindrical stem having a distal end from which said legs extend distally and radially outward.

10. A suture tie device as recited in claim 9 wherein said collar defines a central opening for receiving said stem and legs and a plurality of engaging members are formed along at least a portion of an exterior surface of said stem and legs and along an inner surface of said opening to permit distal movement of said collar from said stem onto said legs to gather said plurality of legs radially inward.

11. A suture tie device as recited in claim 10 wherein a recess is formed on a distal face of said collar to receive said sharp tissue penetrating tips of said outwardly turned hooks.

12. A suture tie device as recited in claim 11 wherein said recess is a cylindrical cavity.

13. A suture tie device as recited in claim 8 wherein said collar defines a plurality of openings each of which is configured to receive one of said legs.

14. A suture tie device as recited in claim 13 wherein said legs extend distally and radially outward from said plurality of openings and a plurality of engaging members are formed along at least a portion of an exterior surface of said legs and along respective inner surfaces of said openings to permit distal movement of said collar on said legs to gather said plurality of legs radially inward.

15. A suture tie device as recited in claim 1 wherein at least a portion of said outwardly turned hooks, leg means and collar are made of a bioabsorbable material.

16. An applicator in combination with a suture tie device, the applicator being applicable for use in applying the suture tie device to anatomical tissue, the suture tie device having at least two outwardly turned hooks emanating from at least one leg and a collar movable along the leg toward sharp tissue penetrating tips of the outwardly turned hooks, the applicator comprising an elongate tubular housing having a proximal portion and a distal portion for holding the suture tie device;

leg controlling means, coupled with a proximal end of said at least one leg, for controlling proximal and distal movement of said at least one leg; and collar displacing means, abutting a proximal face of said collar, for selectively displacing said collar along said at least one leg toward said tissue penetrating tips of said hooks.

17. An applicator as recited in claim 16 wherein said collar displacing means includes an elongate tubular sleeve telescopically disposed within said tubular housing and said leg controlling means includes a rod translatably disposed within a bore defined in said elongate tubular sleeve.

18. An applicator as recited in claim 17 wherein at least one elongated longitudinal slot is formed in a proximal end of said tubular sleeve and said rod includes at least one radially extending arm engaged in said longitudinal slot.

19. An applicator as recited in claim 18 wherein said radially extending arm is biased towards a distal end of said longitudinal slot.

20. An applicator as recited in claim 19 wherein said tubular sleeve protrudes from a proximal end of said housing and said elongate tubular housing includes a finger grip defined near a proximal end of said housing to facilitate grasping.

21. An applicator as recited in claim 20 wherein said finger grip is an outwardly extending flange.

22. An applicator as recited in claim 20 wherein said finger grip is a reduced diameter portion defined near a proximal end of said elongate tubular housing to facilitate grasping.

23. An applicator as recited in claim 22 wherein said tubular sleeve includes a reduced diameter proximal portion extending proximally through said reduced diameter portion of said elongate tubular housing.

24. An applicator as recited in claim 23 wherein the proximal end of said housing is closed around said reduced diameter portion of said sleeve and said rod terminates proximally between said reduced diameter portion of said housing and said closed proximal end of said housing.

25. An applicator as recited in claim 24 and further comprising a scale marked on a proximal portion of said tubular sleeve in the vicinity of said longitudinal slot to indicate an extent of movement of said rod relative to said tubular sleeve.

26. An applicator as recited in claim 20 wherein said finger grip is defined by a pair of longitudinally spaced, outwardly extending flanges provided near a proximal end of said elongate tubular housing to facilitate grasping.

27. An applicator as recited in claim 26 wherein an increased diameter bore portion is defined in a proximal end of said tubular sleeve and said rod includes an increased diameter portion which is disposed within said increased diameter bore portion of said tubular sleeve.

28. An applicator as recited in claim 27 wherein at least one longitudinally extending cavity is defined in an inner wall of said elongate tubular housing near a proximal end to receive said at least one radial arm of said rod.

29. An applicator as recited in claim 28 wherein a scale is marked on a proximal portion of said tubular sleeve to indicate an extent of movement of said rod relative to said tubular sleeve.

30. An applicator as recited in claim 20 wherein said rod and radial arm protrude from a proximal end of said tubular housing.

31. An applicator as recited in claim 30 and further comprising a scale marked on a proximal portion of said tubular sleeve in the vicinity of said longitudinal slot to indicate an extent of movement of said rod relative to said tubular sleeve.

32. An applicator as recited in claim 31 wherein said at least one leg of said suture device and said rod are coupled with a frangible, bioabsorbable pin.

33. A method of suturing anatomical tissue proximate an opening comprising the steps of positioning within the opening a suture tie device with leg means for supporting at a distal end at least two outwardly turned hooks having sharp tissue penetrating tips;

penetrating tissue proximate the opening with said sharp tissue penetrating tips of said outwardly turned hooks; and moving a collar distally along the leg means towards the sharp tissue penetrating tips of the hooks.

34. A method of suturing anatomical tissue as recited in claim 33 wherein said leg means includes a plurality of distally and radially extending legs and further comprising, after said penetrating step, the step of gathering said plurality of legs radially inward.

35. A method of suturing anatomical tissue as recited in claim 33 and further comprising, after said moving step, the step of capturing said sharp tissue penetrating tips of said hooks within at least one recesses formed in said collar.

36. A method of suturing anatomical tissue as recited in claim 35 and further comprising, after said capturing step, the step of camming said sharp tissue penetrating tips of said hooks radially inward against curved surfaces of said at least one recesses.

37. A method of suturing anatomical tissue as recited in claim 36 and further comprising, before said positioning step, the step of creating a puncture site opening in the wall of an anatomical cavity.

38. A method of suturing anatomical tissue as recited in claim 33 wherein said positioning step includes inserting a tubular housing having a proximal end and a distal end holding the suture tie device through an opening in anatomical tissue and retracting said elongate tubular housing relative to said suture tie device.

39. A method of suturing anatomical tissue as recited in claim 28 and further comprising, after said retracting step, the step of expanding a plurality of said legs radially outward.

* * * * *